United States Patent [19]

Stamler

[11] Patent Number: 4,769,003
[45] Date of Patent: Sep. 6, 1988

[54] WOUND IRRIGATION SPLASHBACK SHIELD

[76] Inventor: Keith Stamler, 120 Via la Circula, Redondo Beach, Calif. 90277

[21] Appl. No.: 86,824

[22] Filed: Aug. 19, 1987

[51] Int. Cl.$^4$ .............................................. A61M 7/00
[52] U.S. Cl. ...................................................... 604/39
[58] Field of Search ............... 604/263, 192, 198, 115, 604/117, 38, 40, 42, 278, 36, 37, 119, 39

[56] References Cited

U.S. PATENT DOCUMENTS

| | | | |
|---|---|---|---|
| 724,913 | 4/1903 | Montgomery | 604/278 |
| 1,934,046 | 11/1933 | Demarchi | 604/115 |
| 2,764,975 | 10/1956 | Greenberg | 604/278 X |
| 2,845,065 | 7/1958 | Gabriel | 604/198 |
| 3,896,810 | 7/1975 | Akiyama | 604/117 |
| 4,692,140 | 9/1987 | Olson | 604/40 |

Primary Examiner—John D. Yasko
Attorney, Agent, or Firm—Andra Finkel

[57] ABSTRACT

An instrument for preventing the splashback of potentially infectious fluids and body tissues during wound irrigation as well as for preventing needle impalement injury to patient or ancillary medical personnel comprises a hub (16) having a central bore (18) the proximal end of which will accept the tip of a syringe (14) and which is integrally joined to a narrow diameter tubule (22) extending from the distal end, said tubule being directed down the central longitudinal axis of a transparent, dome-shaped shield (24). Said shield is integrally joined at its proximal end around the hub and gradually enlarges in diameter towards its distal end, terminating in a circular rim (36). Said shield, when placed adjacent to a wound (40) to be irrigated, will effectively contain potentially infectious splashback (46) and prevent said splashback from contacting irrigator or other personnel, as well as protecting the patient and medical personnel from impalement injury due to contact with a needle.

12 Claims, 4 Drawing Sheets

WOUND IRRIGATION SPLASHBACK SHIELD

BACKGROUND-FIELD OF THE INVENTION

This invention relates to medical instruments, especially to a device for the prevention of infectious patient body fluids and tissues from splashing back onto the bodies of medical personnel during wound irrigation.

BACKGROUND-DESCRIPTION OF THE PRIOR ART

In medicine, lacerations must be cleansed prior to closure for two reasons. First, many lacerations are contaminated to some extent by foreign matter, including grass, road particles, grease, animal or human saliva, and the like, and all lacerations are soon colonized by a myriad of bacteria. All of these contaminants will foster infection if debridement is not effective. Second, after the initial cleansing to remove the aforementioned contaminants, the constant ingress of blood hinders wound exploration and closure by obscuring visualization of vital structures. Thus, both before wound exploration and again during closure, meticulous cleansing of the wound is essential.

The method of cleansing which is currently nearly universally employed is irrigation using a disposable syringe and hypodermic needle. The intent is to produce an irrigation stream to mechanically dislodge and remove contaminants and blood. Typically, the syringe is filled with the irrigating solution, and the wound is irrigated at a distance of 5 to 25 cm. Although this method is very effective for debriding and cleansing a wound, several drawbacks exist.

The great majority of the irrigation fluid, after it has been injected into the wound, splashes back retrograde from the wound, carrying with it the same blood and contaminants it was used to dislodge. The splashback typically sprays the irrigator and nearby personnel with large palpable droplets. In addition, the irrigation produces a fine mist which may remain suspended in the air for many minutes and spread over an even larger area.

In recent years, both hepatitis B and AIDS (the acquired immune deficiency syndrome) have been transmitted via these droplets carrying these diseases from an infected patient into the eyes, mouth or skin break of a non-infected person. Although some physicians and dentists are taking precautions, they require the use of goggles and facemasks, which are both cumbersome to the physician and intimidating to the patient. In addition, of course, these offer no protection to bystanders from the fine mist. Clearly a superior method for transmission of these diseases is urgently needed.

Further, similar episodes of disease transmission have been documented due to accidental prick from the needle used in this syringe-needle combination method of wound irrigation. This occurs because the syringe requires multiple refillings of irrigant, each time requiring removing the needle from and replacing it onto the syringe tip. Accidental pricks will occur.

As an aside, despite the widespread use of "sharps" containers in hospitals (puncture-proof conainers exclusively for the disposal of needles, scalpel blades, etc.), delayed skin pricks occur from careless disposal of needles into trashcans, the liners of which are easily punctured by the sharp needles, thus exposing janitorial personnel to needle pricks.

Finally, a separate problem occurs occasionally with the use of the syringe-needle irrigation system. That is dislodgement of the needle from the tip of the syringe due to the high pressure irrigation. Usually, the needle shoots off the tip of the syringe, harmlessly embedding itself into the anesthetized area of the laceration. Should dislodgement occur during irrigation around a highly vulnerable area, i.e. the eye, a catastrophe would occur.

A search of the printed material has failed to disclose any sort of device which addresses all these problems. Although the use of blunt-tipped needles or flexible catheters would prevent needle pricks, and reduce an eye injury, these two methods are almost never used. Obviously, neither would help to contain the splashback and mist which occurs with irrigation, and thus neither would help abate the spread of AIDS and other infectious diseases.

SUMMARY OF THE INVENTION

The invention is a device for restraining the splashback of potentially infectious irrigation fluids comprising, in combination, a conduit and a shield. The conduit for transmitting the irrigation fluid has a proximal hub with a central bore therethrough, as a means for reversible attachment to an injecting means and a linearly contiguous distal nozzle or tubule to create and direct a fine, high-pressure stream of the irrigation fluid. The injecting means may consist of a standard hypodermic syringe, or, if desired, a luer-lock tipped syringe, with the proximal hub of the conduit further having radially extending flanges to allow attachment of this type of syringe. Additionally, the injecting means could be a gravity or electrically pumped irrigation device.

The small end or stem of a transparent shield integrally surrounds the conduit such that the conduit pierces the small end, the proximal hub of the conduit being without and the distal nozzle or tubule being within the shield. The shield enlarges distally to form a larger, open, distal end, the tip of the tubule being recessed from this distal end, in the interior of the shield. The shape of the shield is variable, and might embody, for example, a funnel, a parabolic dome, or a truncated cone, all of which might flare at the larger end by virtue of a distal shoulder. The open distal end will describe a circular or elliptical circumference and the plane of the rim of the distal opening may be perpendicular or oblique to the longitudinal axis of the shield.

The tubule directs the injected fluid generally down the central longitudinal axis of the shield, to impact a wound positioned approximately at the center of the area encompassed by the rim. Thus, reflected fluids and blood will be restrained by the shield, rather than splash onto, and infect surrounding personnel. Additionally, the use of the invention will preclude the possibility of needle-induced injury to the irrigator, patient, or janitorial personnel.

OBJECTS AND ADVANTAGES

Accordingly, several objects and advantages of my invention are:

to provide an instrument for easily, reliably, and effectively allowing irrigation of a wound, while containing the splashback or ricocheting of irrigation fluid, and preventing this fluid, which is contaminated with potentially infectious body fluids and tissues, from contacting the eyes, mucus membranes or areas of skin disruption of the irrigator or other nearby personnel, to provide a tool which requires a minimum of skill and training to use, and, to provide a tool which is inexpensive to manufacture and sterilize for single patient use.

In addition, further objects and advantages of my invention are:

to provide an instrument which will prevent impalement injury to a patient from puncture due to accidental dislodgement of the needle from the syringe in the combination currently used during pressure irrigation of a wound and, to provide an instrument to eliminate the need for irrigator contact with, and therefore possible skin prick by the needle during removal from and replacement onto the syringe during repeated irrigations using the aforementioned combination.

Readers will find further objects and advantages of the invention from a consideration of the ensuing description and the accompanying drawings.

LIST OF REFERENCE NUMERALS

Irrigator eye
Syringe
Tip of 12
Hub
Bore in 16
Flange of 16
Tubule
Shield
Stem of 24
Proximal shoulder of 24
Body of 24
Flare of 24
Distal shoulder of 24
Rim of 24
Patient skin surface
Wound
Irrigation fluid
Stream of 42
Splashback of 42
Plunger of 12

DESCRIPTION OF THE PREFERRED EMBODIMENT

Figure 1:
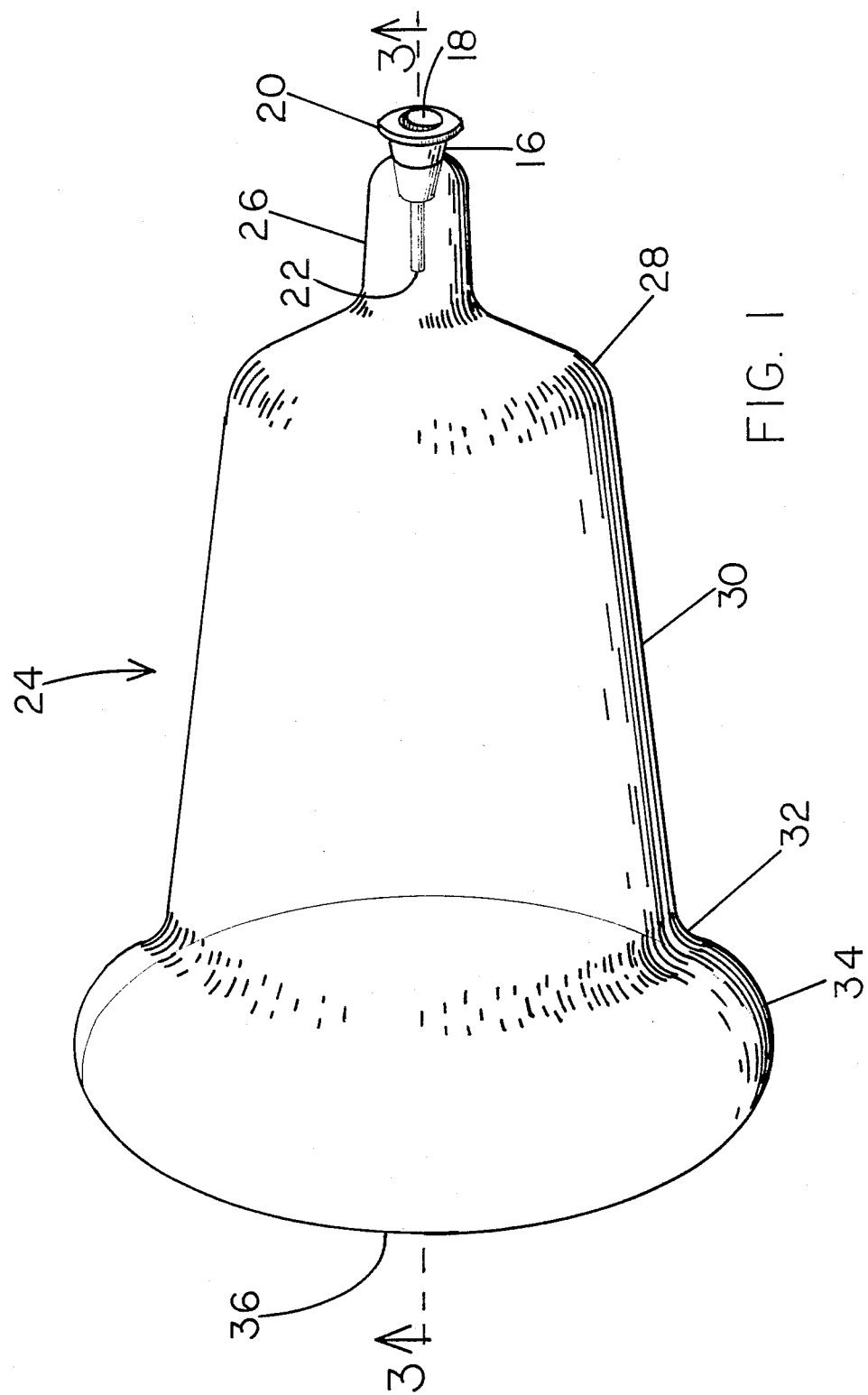
FIG. 1 shows a perspective view of an instrument according to the invention.
Figure 2:
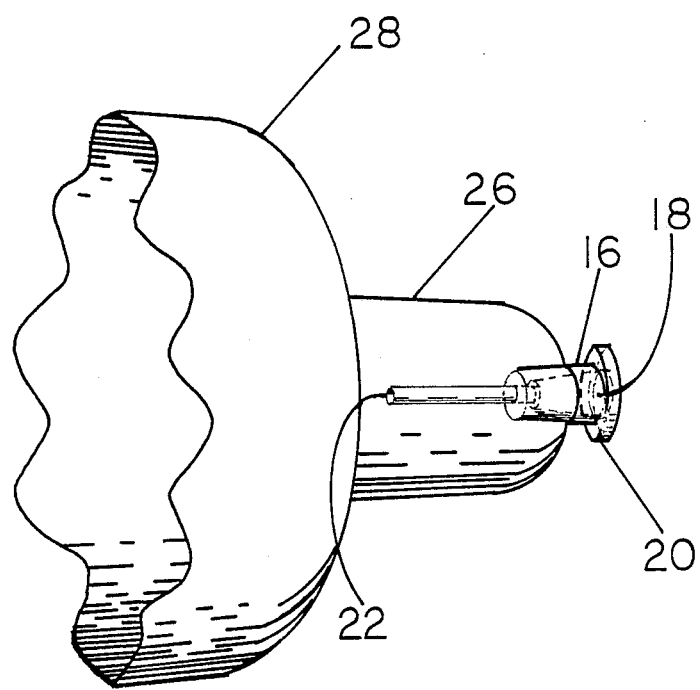
FIG. 2 shows a partially cut-away view of such an instrument
Figure 4:
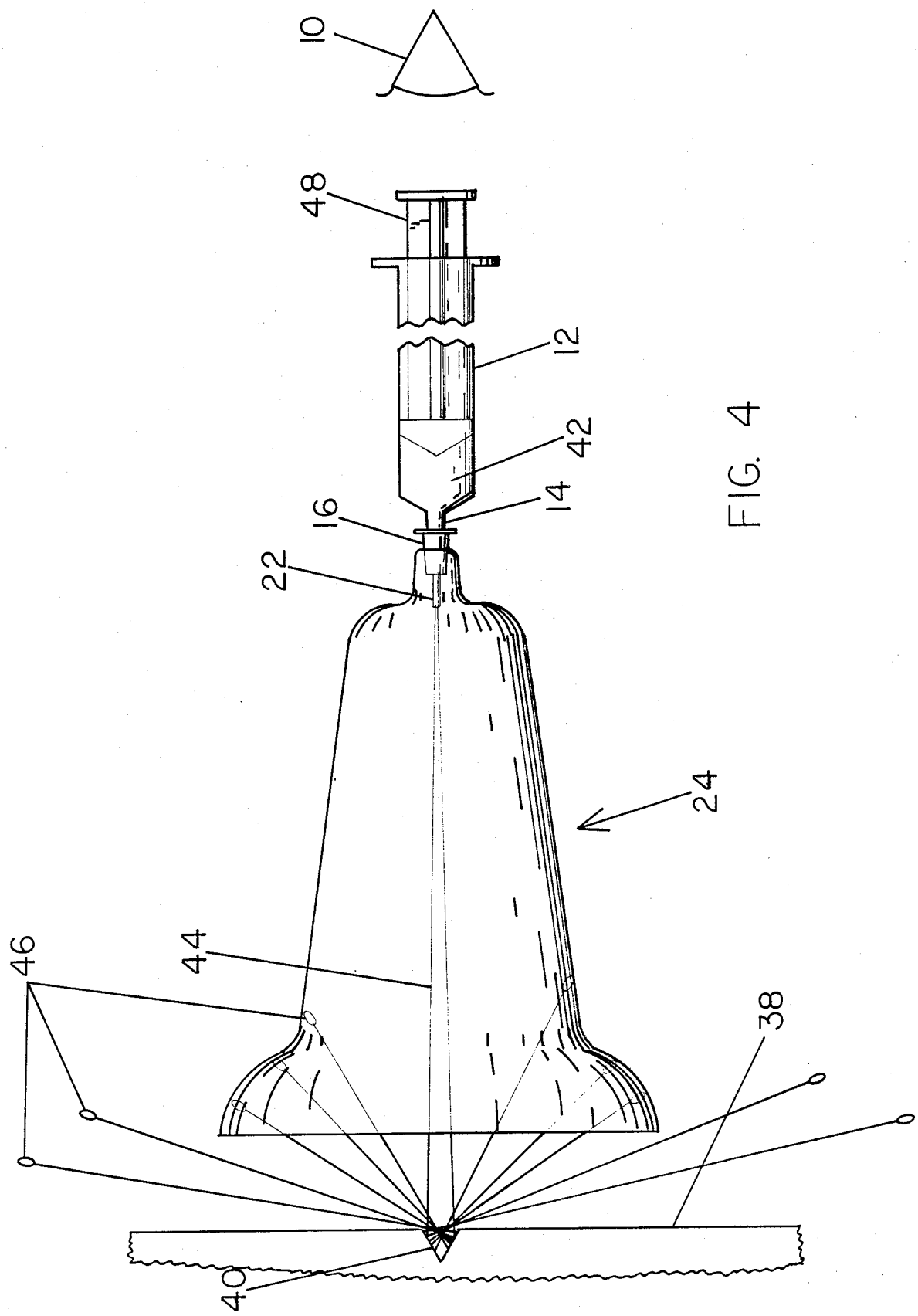
FIG. 4 shows a plan view of such an instrument in use attached to the tip of a luer-tip syringe.

Referring first to FIGS. 1 and 4, the preferred embodiment of the invention is shown. The instrument 24 comprises a plastic hub 16 approximately 1 cm. long, having a slightly tapering central bore 18 in its proximal end. The dimensions of bore 18 correspond to and allow frictional, removable insertion of a luer tip 14 of a syringe 12. As shown in FIG. 4. The flanges 20 which extend radially outward from the free proximal end of the hub 16, allow use of and correspond to reversibly engage a luer-lock syringe tip, not shown. Protruding from the distal end of the hub 16 extends a thin-walled, hollow tubule 22, approximately 5 mm long, the proximal end of which is integral with the distal end of the hub 16, and the central lumen of which is in continuity with the central bore 18 of the hub 16. This tubule 22 is directed along the central longitudinal axis of the surrounding shield 24. The stem 26 of this shield is molded around and is integral with the outside surface of the hub 16 at approximately the midpoint of the length of the hub 16 such that sufficient hub 16 protrudes outward from the stem 26 to allow attatchment of a luerlock syringe tip, if desired.

Figure 3:
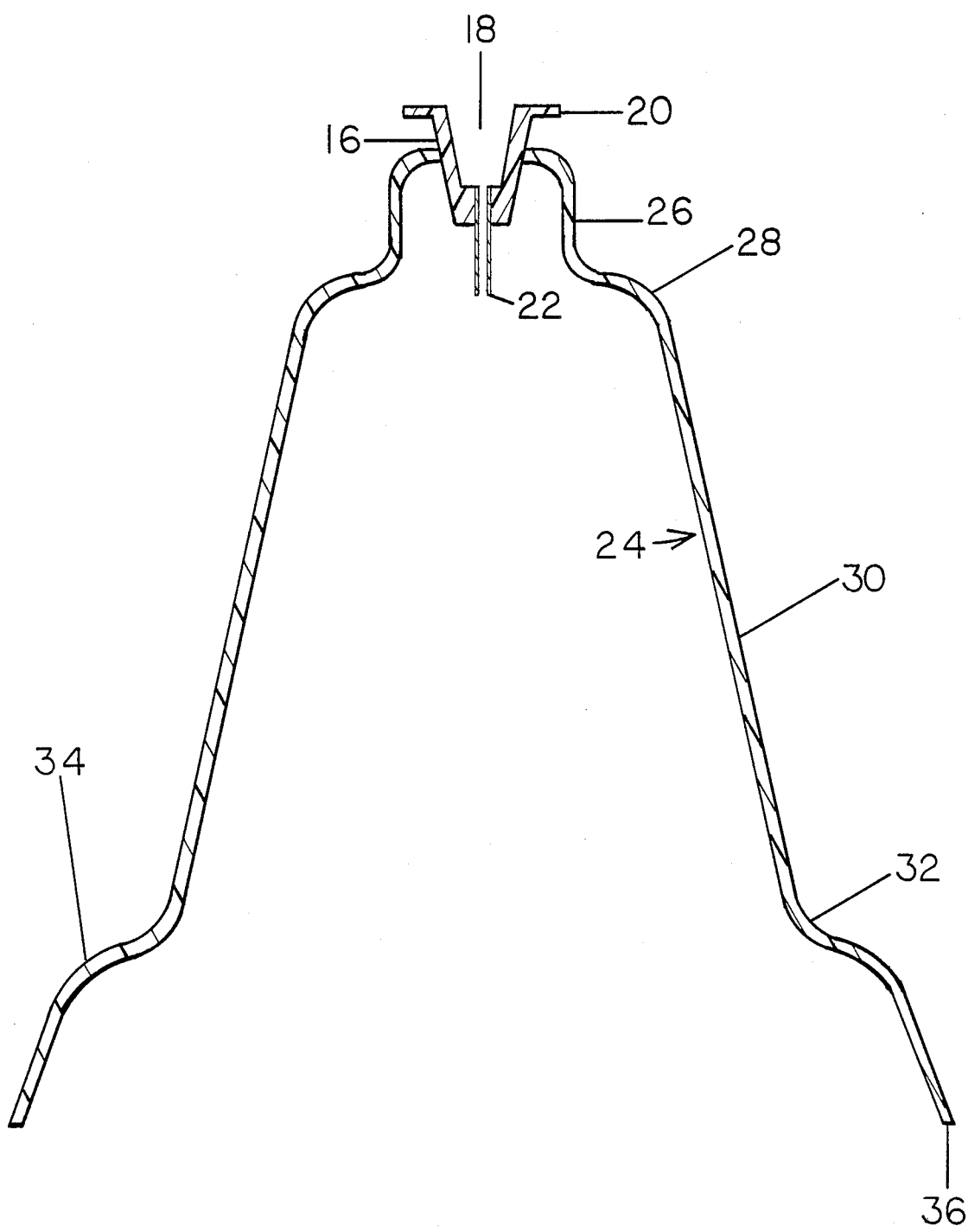
FIG. 3 shows a cross-sectional view along the midline 3—3.

Shield 24, made of transparent material, is a parabolic dome comprising a stem 26, approximately 1 cm. in diameter and 1 cm. in length. Moving distally, this quickly widens in diameter to form the proximal shoulder 28, approximately 1 cm. in length and 3 cm. in diameter, best shown in FIG. 3. The proximal shoulder 28, then becomes the body 30, approximately 8 cm. long which gradually widens in diameter to 5 cm. At this point, the body 30 becomes the flare 32, whence the shield 24 widens more quickly to become the distal shoulder 34, also best shown in FIG. 3. The distal shoulder 34 continues to widen in diameter with convexity outward for approximately 2 cm. to end in the rim 36, which has a final diameter of approximately 9 cm. It can be seen that the distance from the free distal end of the tubule 22 is approximately 12 cm. from the rim of the shield.

OPERATION OF THE PREFERRED EMBODIMENT

The operation of the preferred embodiment of the invention as described, that is to shield the irrigator and nearby personnel from splashback, is best depicted in FIG. 4. A syringe 12 containing irrigation fluid 42 is reversibly attached to the invention by frictionally inserting syringe tip 14 snugly into hub bore 18. If a luerlock type syringe is used, the flanges 20 of the hub 16 will be engaged by using a twisting motion of inserting the syringe 12. The irrigator then places the syringe-invention complex in close proximity to a wound 40 to be irrigated, either directly above, obliquely above, or laterally adjacent to said wound 40, depending on the location and anatomy of the involved patient skin surface 38. In so doing, the rim 36 of the shield 24 will be the closest part of the invention to the skin surface 38, as shown in FIG. 4, most commonly 1 to 3 cm. from said skin surface 38. If properly located, the invention should be oriented such that the wound 40 is located at the approximate center of the circle formed by the rim 36. This will ensure that the tubule 22, being directed down the central longitudinal axis of the shield 24, will then be pointing directly at the wound 40.

Then, by applying pressure to the plunger 42, the irrigation fluid 42 will exit the syringe tip 14, enter the bore 18, continue into the tubule 22, and by virtue of the smaller diameter of said tubule 22 relative to the syringe 12, will then form a narrow, high pressure irrigation stream 44 which will shoot down the central longitudinal axis of the shield 24 and impact and thereby irrigate the wound 40. Due to the high pressure of the irrigating stream 44, a large amount of contaminated and potentially infectious splashback 46 of irrigation fluid will result. The splashback 46, however, rather than reaching and contacting a vulnerable body surface or mucous membrane of the irrigator or other nearby person, represented as the eye 10, will instead be contained within the distal shoulder 34, body 30, and to a lesser extent proximal shoulder 28 of the shield 24. At this point the splashback 46 will drip harmlessly onto the patient skin surface 38.

After exhausting the supply of irrigation fluid 42 in the syringe 12, which in practice takes only 3 to 10 seconds, the syringe 12 will be removed from the invention by detaching the syringe tip 14 from the hub bore 18, and refilling the syringe 12 with irrigation fluid 42. In this manner it can be seen that the invention prevents the contaminated splashback from contacting the irrigator of other personnel. Further, the irrigator never needs contact a sharp object of any sort. Additionally, it can be seen that should the syringe tip 14 become disengaged from the hub 16 during irrigation, only the non-injurious rim 36 of the shield will strike the patient skin surface 38, causing no harm.

While the above description contains many specificities, the reader should not construe these as limitations on the scope of the invention, but merely as exemplifications of the preferred embodiment thereof. Those skilled in the art will envision many possible variations. For example, skilled artisans will note that the hub might be made of metal, and the tubule might be made of plastic, metal or Teflon, a registered trademark of the DuPont Corporation. The tubule can vary in length and diameter, and in fact, the actual manufactured embodiments of the invention would include individual units, each with one of a plurality of tubule diameters, with the individual unit being selected depending on the suitability of the size of the tubule therein to the size and nature of the wound involved Additionally, the shield can be made of any transparent material, including but not limited, to glass, plastic, or acrylic. Variations on the length, diameter, and exact contour of the shield would also be apparent to those skilled in the art. Even the orientation of the rim is variable, such that the plane of the rim could be oblique, rather than perpendicular to the longitudinal axis of the shield, to accomodate different irrigator-patient logistics. Accordingly, the reader is requested to determine the scope of the invention by the appended claims and their legal equivalents and not by the examples which have been described.

I claim:

1. An instrument for restraint of reflected fluids and for monitoring their flow comprising:
    a conduit for transmission of the fluids having a proximal end and a distal end,
    a means for reversibly attaching the proximal end of said conduit to a dispenser of the fluids comprising a proximally protruding plastic cylinder having a central bore, the diameter and depth of said bore corresponding to reversibly accept the tip of a standard, disposably hypodermic syringe and a plurality of flanges extending radially outward, and being oriented perpendicularly to the long axis of said bore, whereby reversible attachment of the tip of a luer-lock syringe may be accomplished, and,
    a generally transparent dome-shaped member with a smaller proximal end integrally surrounding said attaching means, and enlarging substantially vertically and distally to a larger open end, said distal end of said conduit projecting toward the center of an area encompassed by said distal open end of said dome-shaped member, whereby when the fluids, are ejected from said distal end of said conduit, they are directed toward the center of said encompassed area, and after striking a surface within said encompassed area, will be reflected into and restrained by said dome-shaped member such that the reflected fluids will flow down the sides and maintain visualization of the encompassed area.

2. An instrument for safer irrigation comprising:
    a transparent, generally dome-shaped member, having a larger, open, distal end, a smaller proximal end and an inner and outer surface,
    a tubular conduit, said conduit comprising a proximal end protruding exteriorly from the outer surface of said proximal end of said dome-shaped member, said proximal end of said conduit having means for attaching to a fluid containment device comprising a protruding member having a central bore, the diameter, depth, and configuration of said bore corresponding to reversibly accept the exit end of the fluid containment device, wherein said conduit narrows distally to form an elongated tubule, the hollow center of which is linearly fluid contiguous with said central bore of said generally cylindrical member,
    the distal end of said conduit extending into the proximal end of said dome-shaped member, and being recessed therein, said narrow distal end of said conduit being oriented generally along the central longitudinal axis of said dome-shaped member, whereby the fluid ejected from said distal end of said conduit will be directed generally along said central longitudinal axis and whereby when the fluids are ejected from said distal end of said conduit, they are directed toward the center of an area on a surface, and after striking the area of said surface, will be reflected back into and restrained by said dome-shaped member such that the reflected fluids will flow down the sides and maintain visualization of the location of the fluids on the area and whereby the fluid containment device may contact the area.

3. The dome-shaped member of claim 2 wherein the distal portion of said member flares outward to form a distal shoulder with convexity outward, the free edge of said distal portion forming a plane which is perpendicular to the longitudinal axis of said member.

4. The dome-shaped member of claim 2 the distal edge describes a plane which is oblique to the longitudinal axis of said member.

5. The dome-shaped member of claim 3 wherein the shape of said member comprises a truncated cone.

6. The attaching means of claim 2 wherein the proximal free end of said cylindrical member comprises a plurality of flanges extending radially outward, whereby reversible attachment of the tip of a luerlock fluid containment device may be accomplished.

7. An instrument for containing any splashback or spray created when an injectant is directed at an area on a surface for use with a syringe or other injection means, while being able to monitor the direction and flow of the injectant, comprising:
    a transparent substantially rigid bell-shaped means for covering an area on surface having an upper surface, a first opening in said upper surface and an outer rim which is placed on or near the surface,
    tunnel means having a channel for directing the flow of the injectant in a stream or spray into the inside of the bell-shaped means, having a first end and a second end,
    means for attaching the bell-shaped means to the syringe or other means for injecting injectant attached to said first end of said tunnel means and to the first opening the upper surface of said bell-shaped means, whereby when an injectant filled syringe or injection means is attached to the attachment means and compressed, the injectant contained therein is directed through the tunnel means into the inside of bell-shaped means at a surface wherein the bell-shaped means contains any splashback or spray created when the injectant contacts the surface and wherein a viewer can monitor the direction and flow of injectant by looking through the transparent bell-shaped means.

8. The instrument of claim 7 wherein said attachment means further comprises a protruding generally cone shaped member having a central bore and a first and a second end, wherein said second end is attached to the first end of said tunnel means.

9. The instrument of claim 8 wherein the shape of said bore corresponds to accept the injection end of the injection means.

10. The instrument of claim 8 wherein the first end of said cone shaped member comprises a plurality of flanges extending radially outward, whereby the tip of a luer-lock syringe may be attached thereto.

11. The instrument of claim 8 wherein the tunnel means comprises an elongated tube whereby the first end is contiguous with said bore of said cone shaped member.

12. The dome-shaped member of claim 7 wherein the distal portion of said member flares outward to form a distal shoulder with convexity outward, the free end of said distal portion forming a plane which is perpendicular to the longitudinal axis of said member.

* * * * *